United States Patent
Nakatani et al.

(10) Patent No.: US 9,029,150 B2
(45) Date of Patent: May 12, 2015

(54) CELL CULTURE SUBSTRATE AND CELL CULTURE METHOD USING SAME

(75) Inventors: Masaya Nakatani, Hyogo (JP); Makoto Takahashi, Osaka (JP); Yoshiki Yamada, Osaka (JO); Takuya Oka, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 13/695,779

(22) PCT Filed: May 10, 2011

(86) PCT No.: PCT/JP2011/002585
§ 371 (c)(1),
(2), (4) Date: Nov. 1, 2012

(87) PCT Pub. No.: WO2011/142117
PCT Pub. Date: Nov. 17, 2011

(65) Prior Publication Data
US 2013/0045536 A1    Feb. 21, 2013

(30) Foreign Application Priority Data

May 11, 2010   (JP) ................................ 2010-108877

(51) Int. Cl.
| | |
|---|---|
| *C12N 5/071* | (2010.01) |
| *C12M 3/00* | (2006.01) |
| *C12M 1/12* | (2006.01) |
| *C12N 5/00* | (2006.01) |

(52) U.S. Cl.
CPC ............. *C12M 25/14* (2013.01); *C12N 5/0068* (2013.01); *C12N 2533/12* (2013.01); *C12N 2535/00* (2013.01)

(58) Field of Classification Search
None
See application file for complete search history.

(56) References Cited

U.S. PATENT DOCUMENTS

| | | | |
|---|---|---|---|
| 2008/0009043 A1 | 1/2008 | Yoo et al. | |
| 2008/0213851 A1* | 9/2008 | Muller et al. | ................. 435/168 |
| 2009/0191632 A1 | 7/2009 | Fadeev et al. | |

(Continued)

FOREIGN PATENT DOCUMENTS

| | | |
|---|---|---|
| JP | 60-027379 A | 2/1985 |
| JP | 2003-079360 A | 3/2003 |

(Continued)

OTHER PUBLICATIONS

Brillo®, Brillo® Steel Wool Soap Pads, Accessed Online Jan. 14, 2014, at: www.brillo.com/steel-wool-soap-pads.asp.*

(Continued)

*Primary Examiner* — Karen Cochrane Carlson
*Assistant Examiner* — Jennifer M. H. Tichy
(74) *Attorney, Agent, or Firm* — McDermott Will & Emery LLLP

(57) ABSTRACT

The present invention provides a cell culture substrate capable of culturing cells efficiently. The cell culture substrate of the present invention includes a substrate, a plurality of fibrous protrusions formed on the substrate, and water-repellent film formed on a surface of each of the fibrous protrusions. The fibrous protrusions are intertwined with each other to form a matrix structure. According to such a cell culture substrate, when a culture solution containing a specimen is discharged to the water-repellent fibrous protrusions, cells can be cultured easily without contact, thus enabling cells to be cultured efficiently.

15 Claims, 6 Drawing Sheets

(56) References Cited

U.S. PATENT DOCUMENTS

2009/0197333 A1     8/2009    Saito et al.
2010/0331216 A1    12/2010    Sokabe et al.

FOREIGN PATENT DOCUMENTS

| | | | |
|---|---|---|---|
| JP | 2005-061961 A | 3/2005 | |
| JP | 2005-168494 A | 6/2005 | |
| JP | 2005-533509 A | 11/2005 | |
| JP | 2006-223118 A | 8/2006 | |
| JP | WO2006/106748 * | 10/2006 | ............... C12N 5/00 |
| JP | 2006-325532 A | 12/2006 | |
| JP | 2008-011859 A | 1/2008 | |
| JP | 2008-054511 A | 3/2008 | |
| JP | 2008-306987 A | 12/2008 | |
| WO | WO-2006/106748 A1 | 10/2006 | |
| WO | WO-2009/099153 A1 | 8/2009 | |
| WO | WO-2009/099552 A1 | 8/2009 | |

OTHER PUBLICATIONS

Wikipedia, Brillo® Pad, Accessed Jan. 14, 2014, online at: en.wikipedia.org/wiki/Brillo_Pad.*

Wikipedia, Steel Wool, Accessed Jan. 14, 2014, online at: en.wikipedia.org/wiki/Steel_wool.*

Saito et al., WO2006/106748; 2006; machine translation of the document, completed Jul. 22, 2013.*

M.W. Hayman et al., "Enhanced neurite outgrowth by human neurons grown on solid three-dimensional scaffolds" *Biochemical and Biophysical Research Communications* 314 (2004): pp. 483-488.

M.W. Hayman et al., "Growth of human stem cell-derived neurons on solid thre-dimensional polymers" *J. Biochem. Biophys. Methods* 62 (2005): pp. 231-240.

"The Development of Alvetex for 3D Cell Culture" <http://www.reinnervate.com/science/development-alvetex>, Available online: Oct. 3, 2013.

R. Carnachan et al., "Tailoring the morphology of emulsion-templated porous polymers" *Soft Matter* 2 (2006): pp. 608-616.

A. Barbetta et al., "Tailoring the Porosity and Morphology of Gelatin-Methacrylate PolyHIPE Scaffolds for Tissue Engineering Applications" *Langmuir* 21 (2005): pp. 12333-12341.

International Search Report mailed Jul. 19, 2011 issued in corresponding International Application No. PCT/JP2011/002585.

* cited by examiner

CELL CULTURE SUBSTRATE AND CELL CULTURE METHOD USING SAME

RELATED APPLICATIONS

This application is the U.S. National Phase under 35 U.S.C. §371 of International Application No. PCT/JP2011/002585, filed on May 10, 2011, which in turn claims the benefit of Japanese Application No. 2010-108877, filed on May 11, 2010, the disclosures of which Applications are incorporated by reference herein.

TECHNICAL FIELD

The present invention relates to a cell culture substrate used for culturing various cells such as cells derived from blood and cells derived from tissue, or iPS cells and ES cells and to a cell culture method using the same.

BACKGROUND ART

Conventionally, the following method has been used for isolating and culturing cells derived from human and animal sources. Firstly, a culture solution is prepared by adding nutrient such as glucose, a growing agent for promoting growth of a cell, antibiotics for preventing proliferation of miscellaneous bacteria, or the like, into a physiological saline solution. Then, cells are scattered in the culture solution at a predetermined concentration. Then, the culture solution containing cells is placed in a container such as a plane culture dish. Thereafter, the culture dish is set in an environment maintaining device (generally referred to as an incubator) capable of maintaining a surrounding environment. With the environment maintaining device, temperatures, carbon dioxide concentrations, and oxygen concentrations as the surrounding environment of the culture dish are kept at predetermined values and allowed to stand for two to three days so as to wait for division and proliferation of the cells.

The proliferation rate of a cell varies depending upon types, states and environments of a cell. In, for example, RBL (Rat Basophilic Leukemia), the cell concentration becomes about 10 times after three days have passed. At this time, the cell absorbs nutrient necessary for proliferation from a culture solution around the cell and, at the same time, the cell exhausts waste matters. Therefore, the state of the culture solution in the culture dish is largely changed as cell proliferation proceeds. Furthermore, in, for example, CHO (Chinese Hamster Ovary), cells proliferate while they adhere to a plane part of the culture dish. Therefore, when a space to which the cells adhere is lost in the plane part of the culture dish, the proliferation of cells stops. In this way, when the proliferation of cells proceeds, the density of cells in the culture solution is increased, and further proliferation is not carried out. Therefore, after the culture of cells proceeds to some extent, the cells and the culture solution are recovered from the culture dish, and the cells are separated from the culture solution by using a centrifugal separator. Then, an old culture solution is removed, and the cells are scattered on a new culture solution at an appropriate concentration. Thus, cells are newly cultured. This operation is generally called subculture.

In particular, it is important for cell culture that the subculture is appropriately carried out according to a state of a cell. However, in particular, in a case of adhesive cells, in a culture dish having a plane part, the lower parts of the cells are closely attached to the plane part. Consequently, it may be difficult to maintain an environment surrounding cells, in particular, an environment surrounding cells on the surface that is brought into contact with the culture dish.

In order to solve such problems, for example, it is proposed that the contacting degree between a culture dish and cells be reduced by forming a group of minute protrusions on a plane part of a culture dish, thus controlling the close attaching degree (for example, PTL 1 and PTL 2).

Alternatively, it is proposed that a plurality of spherical protruding portions, which have been subjected to water-repellent treatment, are arranged on a rectangular plate with an appropriate spacing, and the protruding portions hold a liquid droplet and a cell be cultured in the liquid droplet (for example, PTL 3).

Cells are sensitive to changes of their surrounding environment. Therefore, as mentioned above, failing to exchange culture solutions or maintain a surrounding environment may cause changes in pH or an oxygen concentration of a culture solution, or may cause waste matters to accumulate in a predetermined place. Thus, the activity of cells in the surrounding in which an undesirable change of environment occurs is lost. Therefore, maintaining of the surrounding environment of a cell is an extremely important factor for cell culture. However, in a conventional plane culture dish, the working efficiency mentioned above is not good. Accordingly, in a cell culture substrate having a conventional configuration and a cell culture method using the same, working efficiency of cell culture is not good.

Each of the techniques shown in PTLs 1 to 3 is one of methods for solving such problems, but has limitations on improvement of working efficiency. In the techniques disclosed in PTLs 1 and 2, a group of protrusions are formed by transferring convex and concave patterns on a substrate by pressing a mold provided with minute convex and concave patterns on a substrate as a culture dish. A so-called nano-imprinting technique is used. Therefore, each of the formed group of protrusions is independent from each other. Consequently, a shape in which protrusions are connected to each other cannot be formed. Furthermore, since a group of protrusions formed by the above-mentioned transfer method can be formed only on the plane of the substrate, only a group of protrusions extending in the direction perpendicular to the plane of the substrate can be configured.

Alternatively, in the technique disclosed in PTL 3, similarly, since a rectangular plane substrate is used as a base material, only protrusions extending in the direction perpendicular to the plane of the substrate can be configured. Therefore, formation of protrusions in minute concave and convex patterns formed on the substrate plane of a culture dish has limitations on improvement in the percentage of voids of the protrusions.

CITATION LIST

Patent Literature

PTL 1: Japanese Patent Application Unexamined Publication No. 2005-168494
PTL 2: Japanese Patent Application Unexamined Publication No. 2006-325522
PTL 3: International Publication No. 2006/106748

SUMMARY OF THE INVENTION

The present invention provides a cell culture substrate with which a cell can be cultured more efficiently than conventionally, and a cell culture method using the same.

A cell culture substrate of the present invention includes a substrate, a plurality of fibrous protrusions formed on the substrate, and a water-repellent film formed on a surface of each of the fibrous protrusions. The plurality of fibrous protrusions are intertwined with each other to form a matrix structure. With such a cell culture substrate, a culture solution containing specimens is discharged to the water-repellent fibrous protrusions, thereby making it easy to culture cells without contact. Thus, cells can be cultured efficiently.

DESCRIPTION OF EMBODIMENTS

Figure 1:
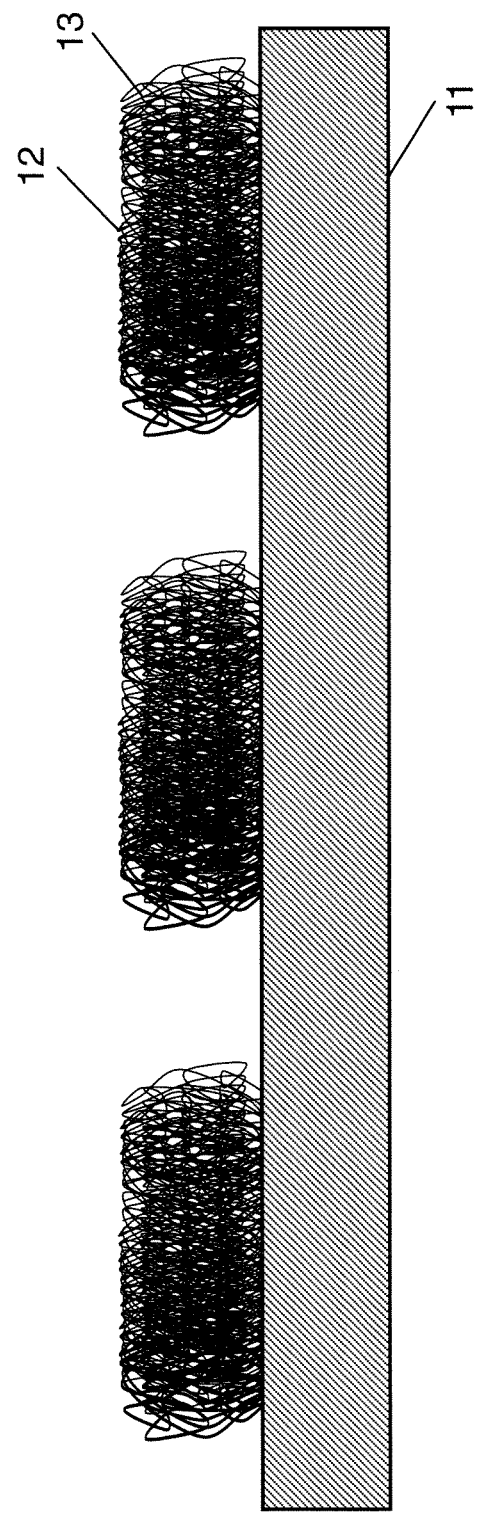
FIG. 1 is a schematic view of a cell culture substrate in accordance with an exemplary embodiment of the present invention.
Figure 2:
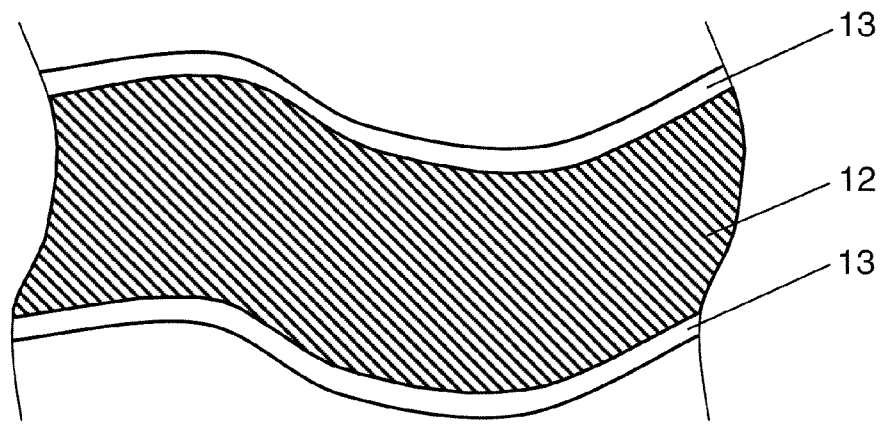
FIG. 2 is an exploded view of a fibrous protrusion of the cell culture substrate in accordance with the exemplary embodiment of the present invention.

FIG. 1 is a schematic view of a cell culture substrate in accordance with this exemplary embodiment. FIG. 2 is an exploded view of a fibrous protrusion in the cell culture substrate of FIG. 1.

As shown in FIG. 1, the cell culture substrate in accordance with this exemplary embodiment includes substrate 11 and a plurality of fibrous protrusions 12. Substrate 11 is, for example, a silicon substrate made of single crystal silicon. Besides this, as substrate 11, for example, polycrystalline silicon and amorphous silicon can be used as a material. Fibrous protrusions 12 are directly joined to substrate 11. The plurality of fibrous protrusions 12 are intertwined with each other to form a matrix structure. Fibrous protrusion 12 includes silicon dioxide as a main component. As shown in FIG. 2, water-repellent film 13 is formed so as to cover an entire surface of fibrous protrusion 12. Water-repellent film 13 includes, for example, carbon fluoride (CF) polymer and is coated on a surface of each of the plurality of fibrous protrusions 12.

The "directly joined" herein denotes a state in which fibrous protrusion 12 is directly formed on substrate 11, and atoms constituting substrate 11 and fibrous protrusion 12 are bonded to each other. In general, it denotes a state in which molecules of fibrous protrusion 12 and substrate 11 are covalently bonded to each other. In this exemplary embodiment, a silicon atom on the surface of substrate 11 and a silicon atom on the surface of fibrous protrusion 12 are covalently bonded to each other via an oxygen atom. Furthermore, the surface on which substrate 11 and fibrous protrusion 12 are joined to each other does not include adhesives and the like, and does not include materials other than atoms or molecules constituting substrate 11 and fibrous protrusion 12.

As mentioned below, substrate 11 and fibrous protrusion 12 may not be necessarily "directly joined" to each other.

The length of fibrous protrusion 12 is about not less than 10 μm and not more than 200 μm in full length. A plurality of fibrous protrusions 12 may be closely formed such that they are intertwined with each other or may be formed by mixing fibrous protrusions 12 that branch in any directions. However, when a plurality of fibrous protrusions 12 are intertwined with each other and branch so as to form a matrix structure, a fiber structure including a plurality of fibrous protrusions 12 is formed strongly. Note here that it is preferable that a thickness of fibrous protrusion 12 is 0.01 μm to 10 μm. When the thickness of fibrous protrusion 12 is more than 10 μm, the percentage of voids per unit area may be reduced. Furthermore, it is preferable that a spacing between fibrous protrusions 12 is preferably 0.001 to 10 μm. When the spacing between fibrous protrusions 12 is larger than 10 μm, an effect of holding a liquid droplet may be reduced.

Figure 3:
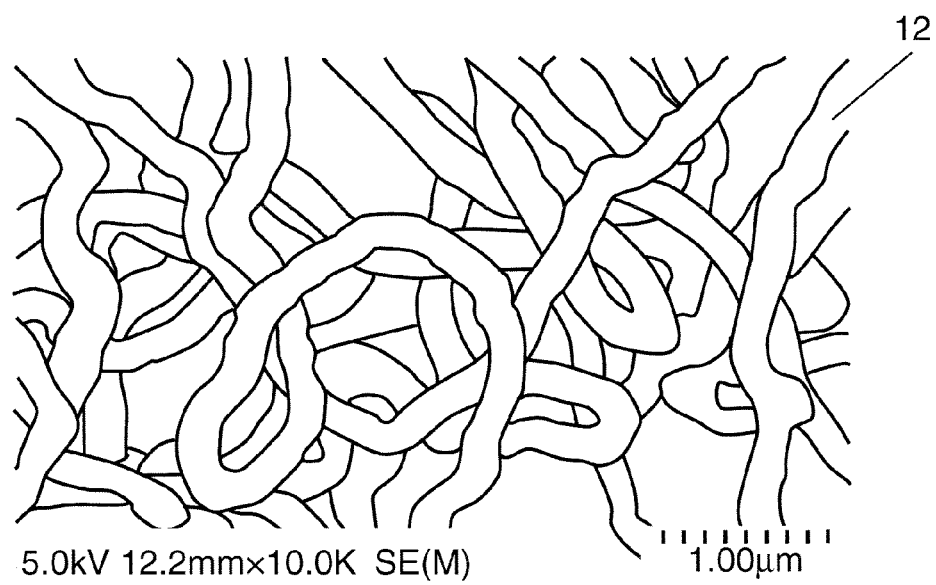
FIG. 3 is a view showing a SEM image of the fibrous protrusions of the cell culture substrate in accordance with the exemplary embodiment of the present invention.

FIG. 3 is a view showing a SEM image of fibrous protrusions 12. Fibrous protrusion 12 includes, for example, silicon oxide including silicon dioxide as a main component, and, in more detail, includes amorphous silicon dioxide as a main component. The number of molecule ratio of silicon and oxygen is about 1:2, but since silicon dioxide is in an amorphous state, the number of molecule ratio may be microscopically displaced depending upon places. Such displacement is not meant to limit the configuration of the present invention. Furthermore, fibrous protrusion 12 may contain a small amount of impurities, but such impurities are not meant to limit the configuration of the present invention. Furthermore, it is preferable that the tip of fibrous protrusion 12 is curved from the direction perpendicular to the substrate plane. This enables a plurality of fibrous protrusions 12 to be intertwined with each other and the density of a plurality of fibrous protrusions 12 to be improved.

Next, an example of a method for manufacturing a cell culture substrate of this exemplary embodiment is described.

Firstly, a method for forming fibrous protrusion 12 made of amorphous silicon dioxide is described.

A Pt layer as a catalyst layer is formed only in a portion in which fibrous protrusions 12 are desired to be formed on substrate 11 made of single crystal silicon. For forming the Pt layer on the surface of substrate 11, general thin film formation such as sputtering, vapor deposition, and spin coating can be employed. It is desirable that the film thickness of Pt is about 1 to 20 nm.

Thereafter, substrate 11 on which the Pt layer is formed is heat-treated at a temperature of 1000 to 1200° C. at an oxygen partial pressure of 0.1 to 1000 Pa in a gas containing an inert gas for a predetermined time. In this heat treatment process, in particular, in a temperature rising process, the Pt thin film formed on substrate 11 is melted and coagulates in a form of particles (particles are not shown). At this time, the particle diameter of the coagulating Pt can be controlled by thickness of the firstly formed Pt film, a temperature rising speed or a temperature during heat treatment, and the like. Furthermore, heating is allowed to proceed and when the temperature reaches a vapor pressure temperature of a material constituting substrate 11, the material is evaporated from substrate 11. Specifically, silicon is evaporated. Then, this evaporated silicon is bonded to oxygen existing in an atmosphere to form silicon suboxide, and the silicon suboxide is vaporized. This vaporized silicon suboxide is supersaturated, and a part thereof is liquefied. The liquefied silicon suboxide coagulates around Pt as a core that has coagulated in a form of particles. The liquefied silicon suboxide that coagulates around Pt is further bonded to oxygen existing in an atmosphere so as to be solidified as silicon dioxide. On the tip of the solidified silicon dioxide, liquefied silicon suboxide further coagulates, and silicon dioxide is further formed. Thus, fibrous protrusion 12 made of silicon dioxide is formed from Pt as a core. Note here that the diameter of fibrous protrusion 12 is affected by the particle diameter of Pt, an oxygen concentration or temperature of the atmosphere, and the like. Therefore, by controlling them, fibrous protrusion 12 having a necessary diameter and a length can be formed on substrate 11.

When productivity and heat resistance of fibrous protrusion 12 are taken into consideration, as heat-treatment conditions, it is more preferable that a temperature is 1100 to 1200° C. and an oxygen partial pressure in a gas containing an inert gas is 10 to 200 Pa. Fibrous protrusion 12 is formed of silicon on the surface of substrate 11 and oxygen gas supplied in the heat treatment process as raw materials. Consequently, the surface of substrate 11 and fibrous protrusions 12 are directly joined to each other and strongly bonded to each other. Furthermore, when the total pressure of an atmosphere of a reaction field is made to be lower than an atmospheric pressure, fibrous protrusions 12 having small distribution of length can be formed.

Note here that fibrous protrusions 12 are formed along the direction in which oxygen gas diffuses in the heat treatment process. In particular, when an oxygen partial pressure value in the atmosphere of a reaction field is high, a plurality of fibrous protrusions 12 closely aggregate in a matrix structure such that they are intertwined with each other and they are made into a curled shape. On the contrary, when the oxygen partial pressure value is low, a plurality of fibrous protrusions 12 are oriented in the same direction.

Note here that fibrous protrusions 12 can be formed such that the tip of each fibrous protrusion 12 is curved from a direction perpendicular to substrate 11 by controlling the conditions in the heat treatment process. Thus, a plurality of fibrous protrusions 12 are intertwined with each other and the density can be improved. Herein, examples of the conditions in the heat treatment process include a gas flow rate, a gas partial pressure, a gas total pressure, a temperature, and an exhaustion speed.

The atmosphere of the reaction field of the heat treatment process is preferably a state in which as much oxygen as possible is removed in a temperature-rising process, and preferably a state of a low oxygen partial pressure in which a small amount of oxygen is added in a temperature maintaining process after the temperature rising. Thus, the productivity of fibrous protrusions 12 is improved.

The high oxygen partial pressure specifically denotes that, for example, an oxygen partial pressure is about 50 to 1000 Pa at the time when the total pressure of a gas containing an inert gas is 1000 to 5000 Pa.

On the other hand, the low oxygen partial pressure specifically denotes that, for example, an oxygen partial pressure is lower than about 50 Pa at the time when the total pressure of a gas containing an inert gas is 1000 to 5000 Pa.

Note here that as a heat-treatment temperature is lower, the oxygen partial pressure suitable for formation of fibrous protrusions 12 becomes smaller. Accordingly, when the temperature rising process is carried out at an oxygen partial pressure suitable for temperatures at the time of the temperature maintaining process, oxygen in the temperature rising process becomes excessive. Then, at the time of temperature rising process, an oxide film may be formed on a Si surface. The oxide film on the Si surface suppresses the formation of fibrous protrusions 12 at the time of the temperature maintaining process.

The above-mentioned process permits controlling of fibrous protrusions 12 in a length of 1 to 500 µm.

Note here that when a layer including silicon dioxide as a main component is formed on a part of the surface of substrate 11 made of silicon, formation of fibrous protrusions 12 from a portion in which the layer is formed can be suppressed. This is because even if a catalyst layer is deposited on the layer including silicon dioxide as a main component, fibrous protrusions 12 are not formed therefrom. Thus, fibrous protrusions 12 can be formed only in a necessary portion on substrate 11.

Furthermore, when a catalyst layer is formed only in a desirable position on the surface of substrate 11 made of silicon, it is also possible to selectively form fibrous protrusions 12 only in a desirable position. This is because the above-mentioned liquefaction of silicon suboxide intensively occurs around the core formed of particles of the catalyst layer.

Note here that Pt is used for the catalyst layer, but the same effect can be obtained when, for example, Fe, Co, Ni, Au, or the like, is used. However, it is desirable that materials used for the catalyst layer are materials that do not easily evaporate at a temperature at the time of formation of fibrous protrusions 12. When the catalyst layer evaporates, the core for promoting the liquefaction of silicon suboxide is lost, so that fibrous protrusions 12 are not easily formed.

Next, a method for coating water-repellent film 13 on the formed fibrous protrusion 12 is described.

Substrate 11 provided with fibrous protrusions 12 is disposed in a vacuum device. Next, a carbon fluoride gas is introduced into the vacuum device. Then, the gas introduced into the device is made into plasma, water-repellent film 13 made of carbon fluoride polymer is coated on the surface of fibrous protrusion 12.

As the carbon fluoride gas, for example, carbon fluoride gases such as $CF_4$, $C_2F_6$, $C_3F_6$, $C_3F_8$, $C_4F_8$, $C_5F_8$, and $CHF_3$ can be used. Besides, water-repellent film 13 can be formed of an alkylsilyl group, a fluorosilyl group, and a long chain alkyl group.

Note here that as a method for making gas into plasma, it is desirable to use ICP (Inductively Coupled Plasma). In ICP, the gas made into plasma is not field-accelerated or deflected by a self-bias effect. Therefore, a polymer film is formed uniformly on the surface of fibrous protrusion 12.

Furthermore, when a contact angle of the thus formed water-repellent film 13 is examined, the contact angle in a general silicon substrate is 103.6°, while a contact angle of fibrous protrusion 12 having a water-repellent property is as large as 146.7°. This shows that the surface of fibrous protrusion 12 can be modified into a super water-repellent surface by surface modification. In the measurement of the above-mentioned contact angle, a liquid droplet is allowed to drop, a boundary between gas and liquid is automatically determined from an image taken by computer via a CCD camera, and curve fitting is carried out. Note here that as water-repellent film 13 in accordance with this exemplary embodiment, it is preferable that culture solution 15 has such a water repellent property as that a spherical liquid droplet is formed when culture solution 15 is discharged onto water-repellent film 13.

Note here that as mentioned above, in addition to the method for making gas into plasma, a method of carrying out coating on the surface of fibrous protrusion 12 by vaporizing a water-repellent raw material by heat is employed. By vaporizing an organic solvent of, for example, alcohol and alkane such as heptane, tetradecane, hexadecane, and pentadekane by heat, water-repellent film 13 is coated on the surface of fibrous protrusion 12. Alternatively, water-repellent film 13 can be coated in which a silane coupling agent is dissolved in an organic solvent. Examples of the silane coupling agent include 3-aminopropyltriethoxysilane, 3-glycidoxypropylt-rimethoxysilane, 3-mercaptopropyl trimethoxysilane, vinyl-torimethoxysilane, 3-mathacryloxypropyltrimethoxysilane, 3-acryloxypropyl trimethoxysilane, 3-isocyanatepropyl tri-ethoxysilane, and the like.

Since the above-mentioned configuration can be made by one time process, productivity is excellent.

In this exemplary embodiment, as a method for forming fibrous protrusion 12, a method of depositing a catalyst layer on substrate 11 is described as an example, but other method may be employed. Another method for forming fibrous protrusion 12 includes, for example, a method for forming fibrous protrusion 12 from a seed layer formed on the surface of substrate 11. The seed layer herein denotes a film containing silicon such as thin film silicon and silicon particles. Therefore, when substrate 11 is silicon, a seed layer is not required to be formed. On the other hand, when substrate 11 is other than silicon, a seed layer is used. When substrate 11 provided with a seed layer is heat-treated in an oxygen atmosphere at 1000° C. to 1100° C., fibrous protrusions 12 are formed. Also with this method, it is possible to obtain a cell culture substrate on which substrate 11 and fibrous protrusions 12 are directly formed.

Furthermore, as another method for forming fibrous protrusion 12, when, for example, silicon particles are used, fibrous protrusion 12 can be formed in the absence of a catalyst. Specifically, by heat-treating silicon particles at a high temperature and at a low oxygen concentration, fibrous protrusion 12 can be formed in the absence of a catalyst. This is because the surface area of the silicon particles is larger relative to the volume, evaporation easily occurs with a small heat capacity and even in the absence of a catalyst, or silicon particles are formed into silicon suboxide and is easily vaporized. Furthermore, when silicon particles are used as the seed layer, such a seed layer makes the surface of substrate 11 have convex and concave portions. Consequently, vaporized silicon suboxide easily coagulates in the convex and concave portions, is bonded with oxygen, and is easily solidified into silicon dioxide. Therefore, even when the catalyst layer and the seed layer, which have been described in the above-mentioned manufacturing method, are not provided, fibrous protrusions 12 of silicon dioxide can be formed.

Silicon particles herein denote particles of, for example, silicon, monoxide silicon, or silicide that is a silicon alloy. It is preferable that the size of the silicon particle is as small as possible, and it is, for example, not larger than 5 μm. This makes it possible to increase an evaporation amount of silicon and to form fibrous protrusions 12 more efficiently. Furthermore, the high temperature is desirably, for example, about 1000 to 1200° C. Note here that when monoxide silicon particles are used, fibrous protrusions 12 can be formed even at about 900° C. that is a lower temperature than the above-mentioned temperature. As the low oxygen concentration, for example, an oxygen partial pressure is desirably about not more than 50 Pa at the time when the total pressure of gas containing an inert gas is 1000 to 5000 Pa.

Note here that adjustment of temperatures is carried out in a state in which oxygen is removed as much as possible in the temperature rising process, and is carried out under low oxygen partial pressure in which a small amount of oxygen is added in the temperature maintaining process after the temperature rising. Thus, productivity of fibrous protrusions 12 is improved.

Furthermore, according to the above-mentioned method, fibrous protrusion 12 is formed of silicon particles and oxygen gas supplied in the heat treatment process as raw materials. That is to say, since a material component of substrate 11 made of silicon is not used as a raw material, the cell culture substrate according to this exemplary embodiment can be formed even if a crystalline silicon wafer and the like is not used as substrate 11. For example, quartz, glass, sapphire, or the like, is employed as substrate 11, fibrous protrusion 12 can be formed on such substrate 11. Thus, the cost can be reduced. Furthermore, when a transparent substrate is used as substrate 11, a transmitted illumination type microscope can be used in observation of a cell under a microscope. Thus, a cell can be observed easily.

Alternatively, once fibrous protrusions 12 are formed on a substrate made of silicon, then, fibrous protrusions 12 can be exfoliated and transferred to another substrate 11. For example, after fibrous protrusions 12 are formed on a substrate made of silicon, a cell culture substrate can be formed by transferring fibrous protrusions 12 to substrate 11 made of glass and the like.

Note here that as substrate 11, by employing a substrate on the surface of which an electrode of ITO (Indium Tin Oxide) is formed, a voltage can be applied while a cell is cultured. Thus, a culture solution can be allowed to flow, a state of a culture solution can be electrically measured, and a state of the culture solution can be controlled with high accuracy.

Alternatively, as substrate 11, a flexible substrate such as a glass fiber sheet can be employed. For example, silicon particles are allowed to be contained in the glass fiber sheet and the like, followed by carrying out the above-mentioned heating process. Thus, fibrous protrusions 12 can be formed.

Furthermore, silicon particles are mixed with a binder or the like, and the silicon particles are disposed only in an arbitrary place by spin coating, printing, an ink jet method, or the like, thus making it easy to form fibrous protrusion 12 only in an arbitrary place.

Note here that in a manufacturing method from the above-mentioned particles, the formed fibrous protrusions 12 may be joined to substrate 11 after they are coated with water-repellent film 13.

Figure 4:
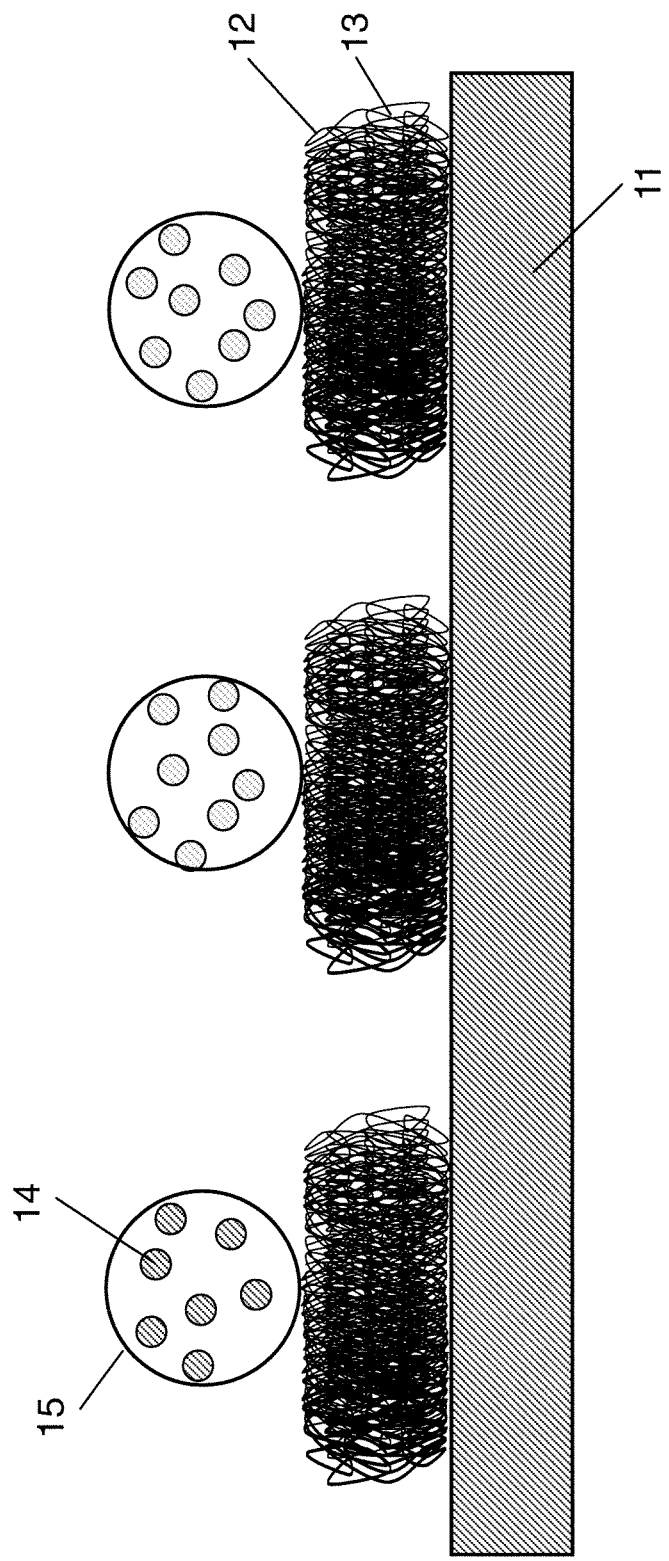
FIG. 4 is a schematic view of the cell culture substrate in accordance with the exemplary embodiment of the present invention.

Next, a cell culture method using a cell culture substrate in accordance with this exemplary embodiment and an effect thereof are described. FIG. 4 is a schematic view of a cell culture substrate in accordance with this exemplary embodiment.

On a plurality of fibrous protrusions 12 formed on substrate 11 in a cell culture substrate, culture solution 15 containing specimens 14 such as cells is discharged. Specimens 14 are planted in culture solution 15 at a predetermined concentration. The cell culture substrate on which culture solution 15 is discharged is set in a predetermined cell culture environment maintaining device. During cell culture, the inside of the cell culture environment maintaining device is kept at a predetermined concentration of a predetermined gas such as oxygen, carbon dioxide, and the like.

Water-repellent film 13 having a super water-repellent property is formed on the surface of each fibrous protrusion 12, and fibrous protrusions 12 are intertwined with each other to form a matrix structure. Therefore, culture solution 15 discharged on fibrous protrusions 12 do not enter a space among fibrous protrusions 12, and are formed in substantially a spherical shape on the upper surface of fibrous protrusions 12. Specimens 14 start to proliferate in culture solution 15. For example, when specimens 14 are adhesive cells, specimens 14 adhere by using a matrix structure made of fibrous protrusions 12 as a scaffold, specimens 14 proliferate in culture solution 15 whose shape is substantially spherical.

That is to say, adhesive cells can proliferate only when they are brought into contact with and fixed to something. When the cells are kept floating, they undergo apoptosis and they may die in many cases. Therefore, for fixing the adhesive cells, something with which they are brought into contact is necessary. However, when the adhesive cells are fixed on the plane part, replacement of culture becomes difficult.

However, in the present invention, since fixation is carried out with respect to a matrix structure formed of fibrous protrusions 12, a necessary area for fixation can be minimized while replacement of media is easily carried out. As a result, this makes proliferation possible.

Furthermore, in the present invention, since the percentage of voids is high, a gas exchange ratio can be improved. Furthermore, a region on a surface of a liquid droplet in which gas is exchanged is finely divided. Thus, gas substitution can be carried out uniformly.

At this time, pH of culture solution 15 is changed by a waste matter as metabolized specimen 14. According to the cell culture substrate of this exemplary embodiment, culture solution 15 does not enter into void portions inside of a fiber structure formed of a plurality of fibrous protrusions 12 by water-repellent film 13 formed on fibrous protrusions 12. Therefore, when the void portions inside of the fiber structure including a plurality of fibrous protrusions 12 are brought into contact with outside air, gas can infiltrate into the void portions abundantly. Consequently, for example, gas can be easily supplied also on the bottom surface of culture solution 15 into which gases such as carbon dioxide and oxygen have not been easily supplied conventionally, thus enabling the entire culture solution 15 to be maintained in a fresh environment. Thus, it is possible to obtain a cell group controlled in an appropriate environment in a process of proliferation of cells.

Note here that when cells used as specimens 14 constitute tissue (for example, skin cells), a cell sheet organized on the upper part of fibrous protrusions 12 can be formed. Also in such a case, since culture solution 15 is in a state in which it does not enter into the void portions but is held on fibrous protrusion 12, culture solutions can be exchanged easily. Thus, the environment of culture solution 15 can be easily held.

Furthermore, since a liquid amount of culture solution 15 is dependent upon the apparent area of the plane part of a fiber structure formed of fibrous protrusions 12, many specimens 14 can be cultured with a large amount of culture solution 15 as an apparent area is larger.

Note here that it is preferable that the tip of each fibrous protrusion 12 is curved from the direction perpendicular to the plane of substrate 11. Thus, a plurality of fibrous protrusions 12 are intertwined with each other with a high density, so that a matrix structure can be configured. Therefore, it is possible to increase an area with which cells can be brought into contact as a scaffold in the top part of the fiber structure formed of fibrous protrusions 12, and sufficient void portions can be held inside the fiber structure. Thus, cells can be cultured more efficiently.

Note here that when external stimulation such as electricity, ultrasonic waves, and vibration is given to cell culture substrate 100, culture solution 15 can be allowed to flow on fibrous protrusions 12. When culture solution 15 is allowed to flow, it is possible to prevent a culture mass from being deposited in culture solution 15, specimens 14 can be cultured in a state in which they are flowing in culture solution 15.

A part of fibrous protrusions 12 may enter into culture solution 15 during cell culture.

Furthermore, according to the cell culture substrate of this exemplary embodiment, differentiation efficiency during cell culture is also improved. In differentiation induction of an iPS cell or an ES cell, the polarity of a cell, that is, arrangement of cytoskeleton molecules such as actin and microtubule is known to be closely involved in cell differentiation. In other words, in the differentiation induction, when the cell adheres to another cell, a support, or the like, the polarity of the cell may be largely affected. Therefore, differentiation induction of a cell without polarity is important for cell culture for forming tissue. In cell culture in, for example, a three-dimensional structure of minute concavities and convexities by a nano-imprinting structure as shown in the conventional example, the cell culture is improved more than culture in a plane. However, due to its structure, cells may be brought into contact with minute concavities and convexities during culture. In many cases, this may bring about polarity in cells. As a result, it becomes difficult to culture cells or to induce differentiation of cells efficiently. However, in the cell culture substrate in this exemplary embodiment, each of a plurality of fibrous protrusions 12 is coated with water-repellent film 13. Then, culture solution 15 containing specimens 14 such as cells can be discharged on the upper surface of fibrous protrusions 12, and cells (specimens 14) are cultured. At this time, specimens 14 are cultured in culture solution 15 in a state in which the entire lower part of specimens 14 is not brought into contact with fibrous protrusions 12. Therefore, since the entire lower part of specimens 14 is not brought into contact with fibrous protrusions 12 during cell culture, efficient cell culture can be carried out. Furthermore, when the diameter of fibrous protrusion 12 can be made to be extremely small, it is possible to further suppress the contact between specimens 14 such as cells and fibrous protrusions 12. At this time, the diameter of fibrous protrusion 12 can be made to be as small as about 10 nm at minimum.

Note here that this exemplary embodiment has features that a matrix structure can be easily formed by fibrous protrusions 12, and in addition, the strength as the fiber structure can be enhanced because connection between fibrous protrusions 12 can be easily carried out, which are features not found in carbon fiber.

Furthermore, for example, by adjusting the density of the matrix structure configured by allowing a plurality of fibrous protrusions 12 to be intertwined with each other, the shape of fibrous protrusion 12 and the percentage of voids can be freely adjusted. Thus, a surface state suitable for each type of a cell treated as specimen 14 can be formed.

Note here that protein may be bonded to a plurality of fibrous protrusions 12 by using SAM (Self Assembly Monolayer) or chemical modification and the like. When protein is bonded, protein enters in culture solution 15, and proliferation of cells can be promoted. The protein herein denotes, for example, actin, albumin, or the like.

Figure 5:
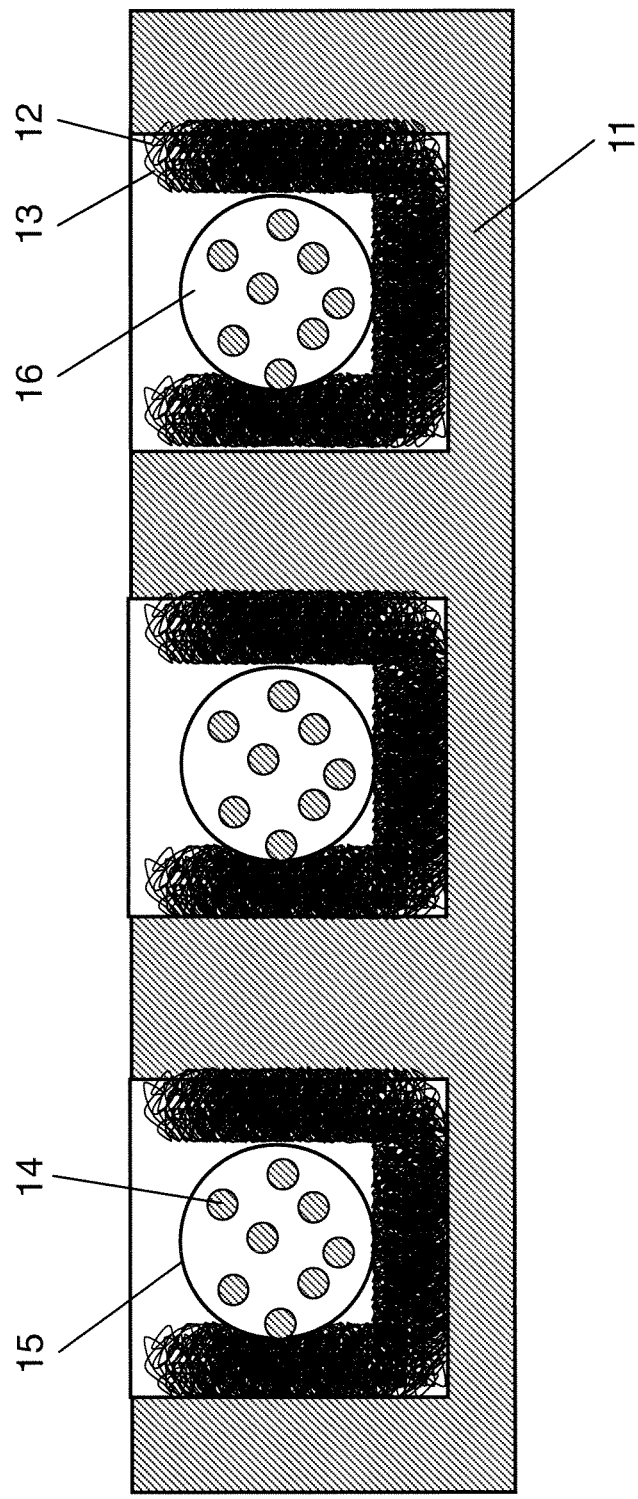
FIG. 5 is a schematic view of another cell culture substrate in accordance with the exemplary embodiment of the present invention.

As shown in FIG. 5, recess 16 having opening may be formed on the surface of substrate 11, and fibrous protrusions 12 may be formed on the inner wall surface of recess 16. On the inner bottom surface and the side surface of recess 16, fibrous protrusions 12 are formed. In addition, the entire surface of fibrous protrusion 12 is coated with water-repellent film 13. In such a cell culture substrate, culture solution 15 discharged on fibrous protrusions 12 formed on recess 16 is held by not only the bottom surface side but also the side surface side. Therefore, for example, even when vibration is applied to substrate 11 during culture, flowing of culture solution 15 and specimens 14 contained therein on the cell culture substrate can be suppressed, thus enabling specimens 14 to be held by the cell culture substrate. Therefore, cells can be cultured more efficiently and reliably.

Figure 6:
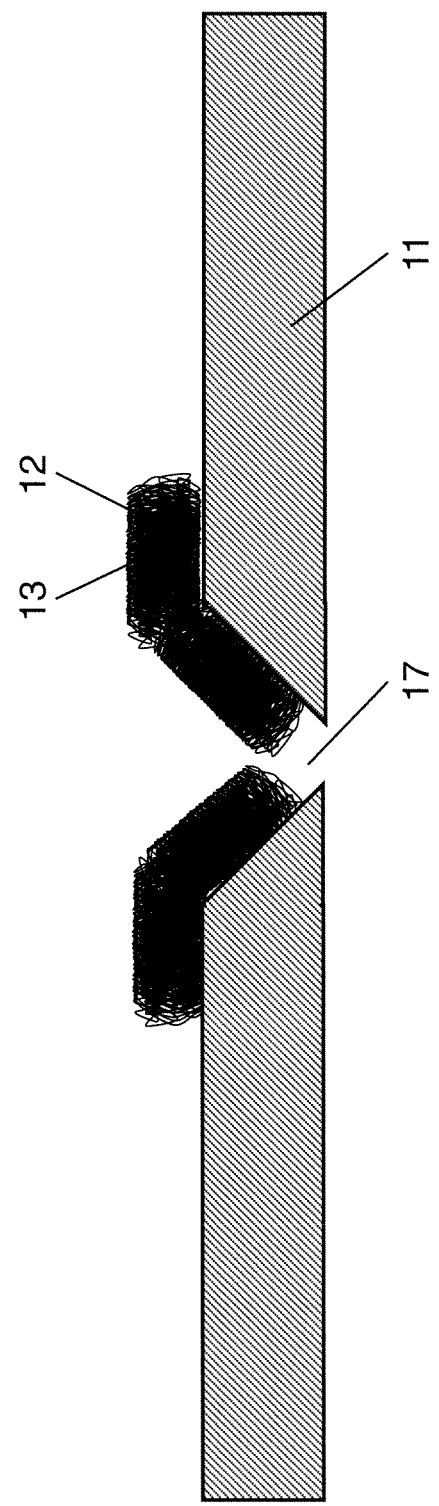
FIG. 6 is a schematic view of still another cell culture substrate in accordance with the exemplary embodiment of the present invention.
Figure 7:
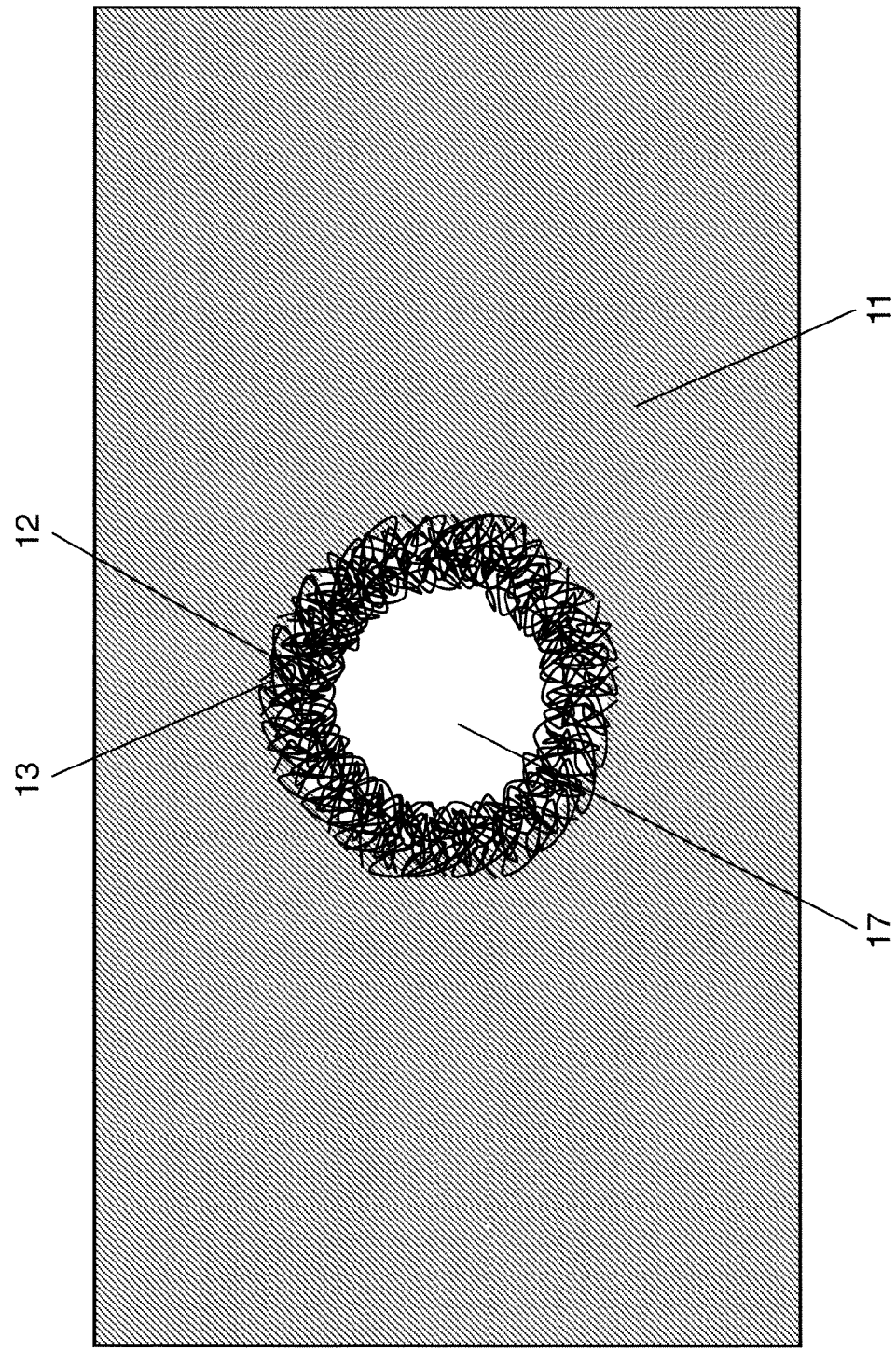
FIG. 7 is a top view of the cell culture substrate shown in FIG. 6.

As shown in FIGS. 6 and 7, substrate 11 may be provided with through hole 17 penetrating through a first surface and a second surface that is opposite surface to the first surface. A plurality of fibrous protrusions 12 are formed from the periphery of through hole 17 in the first surface of substrate 11 to the inner wall surface of through hole 17. Furthermore, the entire surface of each fibrous protrusion 12 is coated with water-repellent film 13.

With the above-mentioned configuration, the side surface of a liquid droplet of culture solution 15 is held by fibrous protrusions 12 and a part of the liquid droplet enters through hole 17. In this way, the liquid droplet is held by the cell culture substrate. Thus, the liquid droplet can be held in a state in which the bottom surface of the liquid droplet is in a perfectly non-contact state. Therefore, cell culture can be carried out while implantation of specimens 14 such as cells is further suppressed. Furthermore, since the bottom surface side of culture solution 15 is opened, observation can be carried out by using an invert microscope. Furthermore, an operation of the liquid droplet of culture solution 15 can be carried out, for example, a drug solution can be input, from the first surface side of substrate 11 while observation is carried out from the second surface side of substrate 11. Thus, a cell can be cultured with higher working efficiency, with reliability, and with higher accuracy.

Note here that as shown in FIG. 6, the shape of through hole 17 preferably have a taper shape such that the hole diameter is narrower from the first surface to the second surface. This is preferable because the liquid droplet of culture solution 15 can be just inserted into and held by through hole 17, so that rolling and movement of the liquid droplet to the other part can be suppressed, and furthermore, dropping to the second surface side of substrate 11 can be suppressed.

Note here that by using a thin plate having a hole for capturing cells at the second surface side of through hole 17, or a patch clamp pipette, for example, it is possible to measure the electrophysiological state of cells in a state in which cells form a network after cell culture.

INDUSTRIAL APPLICABILITY

A cell culture substrate of the present invention is expected to be used for cell culture of cells such as cells derived from blood and cells derived from tissue, or iPS cells and ES cells.

REFERENCE MARKS IN DRAWINGS

11 substrate
12 fibrous protrusion
13 water-repellent film
14 specimen
15 culture solution
16 recess
17 through hole

The invention claimed is:

1. A cell culture substrate comprising:
   a substrate having a first surface and a second surface opposite to the first surface; and
   a fiber structure disposed on the first surface of the substrate, the fiber structure being formed by a plurality of fibrous protrusions, wherein:
   the plurality of fibrous protrusions are made of amorphous silicon dioxide,
   a water-repellent film is disposed on a surface of each of the fibrous protrusions,
   the plurality of fibrous protrusions are three-dimensionally and randomly intertwined with each other to form the fiber structure, and
   the fiber structure includes void portions inside the fiber structure.

2. The cell culture substrate of claim 1,
   wherein each of the plurality of fibrous protrusions bends plural times.

3. The cell culture substrate of claim 1,
   wherein the water-repellent film includes a carbon fluoride polymer.

4. The cell culture substrate of claim 1,
   wherein ends of the plurality of fibrous protrusions and the substrate are directly joined to each other.

5. The cell culture substrate of claim 1,
   wherein the first surface of the substrate has a recess, and the plurality of fibrous protrusions are formed on an inner bottom surface and a side surface of the recess.

6. The cell culture substrate of claim 1, wherein:
   the substrate is provided with a through hole communicating the first surface with the second surface, and
   the fiber structure is formed from a peripheral portion of the through hole in the first surface to an inner wall surface of the through hole.

7. The cell culture substrate of claim 1,
   wherein the water-repellent film is disposed on surfaces of the fibrous protrusions located inside the fiber structure.

8. The cell culture substrate of claim 1,
   wherein a space between the fibrous protrusions is 0.001 μm to 10 μm.

9. The cell culture substrate of claim 1,
   wherein a thickness of at least one of the plurality of fibrous protrusions is 0.01 μm to 10 μm.

10. The cell culture substrate of claim 1,
    wherein the plurality of fibrous protrusions randomly branch.

11. The cell culture substrate of claim 1,
    wherein plural fiber structures, each of which includes the plurality of fibrous protrusions, are separately disposed on the first surface of the substrate.

12. The cell culture substrate of claim 6,
    wherein a shape of the through hole is a taper shape in which a diameter of the through hole becomes narrower from the first surface to the second surface.

13. A cell culture method comprising:
    disposing a culture solution containing a cell on an upper part of the fiber structure of the cell culture substrate of claim 1;
    setting the cell culture substrate in a cell culture environment maintaining device; and
    maintaining an environment such that an inside of the cell culture environment maintaining device has a predetermined gas concentration with gas.

14. The cell culture method of claim 13,
    wherein the gas includes at least any of carbon dioxide and oxygen, and
    the gas is maintained at a predetermined concentration.

15. The cell culture method of claim 13,
    wherein the gas is allowed to circulate in the void portions existing inside the fiber structure.

* * * * *